US005906036A

United States Patent [19]

Pagan

[11] Patent Number: 5,906,036

[45] Date of Patent: May 25, 1999

[54] REINFORCED TUBES

[75] Inventor: Eric Pagan, Hythe, United Kingdom

[73] Assignee: Smiths Industries Public Limited Company, London, United Kingdom

[21] Appl. No.: 08/996,814

[22] Filed: Dec. 23, 1997

[30] Foreign Application Priority Data

Jan. 10, 1997 [GB] United Kingdom .................. 9700428

[51] Int. Cl.[6] .................................................. B23P 17/00

[52] U.S. Cl. ............................ 29/417; 604/527; 29/458; 264/148

[58] Field of Search .................... 29/458, 417; 264/148, 264/149, 150, 171.17, 171.21

[56] References Cited

U.S. PATENT DOCUMENTS

| | | | |
|---|---|---|---|
| 3,485,234 | 12/1969 | Stevens | 128/2 |
| 3,965,909 | 6/1976 | Waddell et al. . | |
| 4,577,543 | 3/1986 | Wilson . | |
| 5,334,169 | 8/1994 | Brown et al. . | |
| 5,421,826 | 6/1995 | Crocker | 604/53 |
| 5,542,926 | 8/1996 | Crocker | 604/102 |
| 5,573,520 | 11/1996 | Schwartz | 604/282 |
| 5,681,296 | 10/1997 | Ishida | 604/282 |

FOREIGN PATENT DOCUMENTS

| | | |
|---|---|---|
| 0 086 498 | 8/1983 | European Pat. Off. . |
| 0 102 422 | 3/1984 | European Pat. Off. . |
| 6-070982 | 5/1994 | Japan . |
| 2009362 | 6/1979 | United Kingdom . |
| 2043201 | 10/1980 | United Kingdom . |

*Primary Examiner*—S. Thomas Hughes
*Assistant Examiner*—Steve Blount
*Attorney, Agent, or Firm*—Pollock, Vande Sande & Amernick

[57] ABSTRACT

Reinforced, cuffed tubes are made by winding a plastic reinforcing filament around the outside of tubing and then applying a flexible layer on top of the tubing to just cover the filament and form a smooth outer surface. The filament is then removed from regions of the tubing using a pick to form a series of reinforced regions and unreinforced regions along the tubing. A second layer is then coextruded over the reinforced and unreinforced regions, which includes a longitudinal lumen. The tubing is cut into tubes midway along the unreinforced regions so that there is an unreinforced region at both ends of the tubes. An inflatable cuff is attached to each tube opening into the lumen in the second layer.

13 Claims, 2 Drawing Sheets

IV
25
24
23
22
21
4
2
4
11
21
IV

REINFORCED TUBES

BACKGROUND OF THE INVENTION

This invention relates to reinforced tubes and methods of forming reinforced tubes.

Medical tubes such as catheters and tracheal tubes can be reinforced, to make them more resistant to crushing, by incorporating a helical reinforcement in the form of a metal wire or a stiff plastic filament. In many cases, however, it is preferable for the tube not to be reinforced at the ends so that these are softer and less traumatic, and so that connection can be made to the tube more easily. There are various ways in which such tubes can be produced. The reinforcing wire or filament could be applied to the tubing only over those regions where reinforcement is required, leaving spaces between the reinforced regions so that the tubing can be cut between the reinforced regions to divide it into separate tubes each with an unreinforced end. Another arrangement, as described in GB 2043201, is to wind a reinforcing wire along the entire length of the tube and to remove the reinforcement by grinding from the regions where the reinforcement is not required. In this latter arrangement, an outer layer is applied on top of tube after removal of the reinforcement.

BRIEF SUMMARY OF THE INVENTION

It is an object of the present invention to provide an improved method of forming reinforced tubes and tubes made by this method.

According to one aspect of the present invention there is provided a method of forming a reinforced tube including the steps of winding a reinforcing element onto the outer surface of a flexible tubular member, applying a first layer of a flexible material to the tubular member substantially level with the outer surface of the reinforcing element, removing the reinforcement element from selected regions of the tubular member to form unreinforced regions intermediate reinforced regions along the tubular member, applying a second layer of a flexible material over the reinforced and unreinforced regions, and cutting the tubular member in said unreinforced regions to divide the tubular member into tubes having at least one unreinforced end.

The reinforcing element may be of rectangular section and is preferably of a plastics material. The first layer is preferably applied by co-extrusion and is of the same material as the tubular member. The second layer is preferably applied by co-extrusion and is of the same material as the first layer. The second layer is preferably formed with a lumen extending along its length. The method may include the step of applying an inflatable cuff to each tube after cutting the tubular member into tubes. The reinforcement element is preferably removed using a pick. The tubular member is preferably cut in the unreinforced regions between the ends of the unreinforced regions so that each tube has two unreinforced ends.

According to another aspect of the present invention there is provided a tube made by a method according to the above one aspect of the invention.

Reinforced tubes and their manufacture, in accordance with the present invention, will now be described, by way of example, with reference to the accompanying drawings.

DETAILED DESCRIPTION OF THE PREFERRED EMBODIMENT

Figure 1:
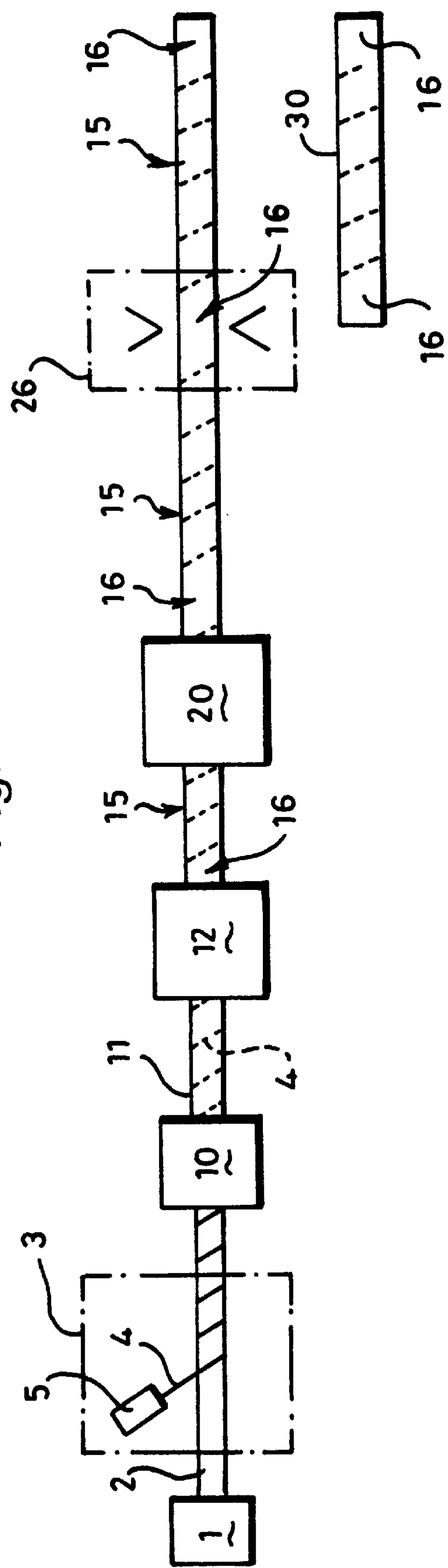
FIG. 1 shows the apparatus schematically.

With reference first to FIG. 1, the apparatus has a tubing extruder 1, which extrudes a continuous tubular member 2, of circular section, of a flexible plastics material such as PVC or polyurethane. Typically, the internal diameter of the tubing ranges from about 2 mm to 11 mm with a wall thickness ranging from about 1 mm to 2.5 mm. Instead of using an extruder, the tubular member 2 could be previously formed, reel stock tubing. The tubular member 2 emerges from the extruder 1 into a reinforcement winding station 3 where a reinforcing element 4 is wound helically about the tubular member. The reinforcing element 4 is carried on a bobbin 5 or the like, or it may be fed directly from an extruder. Preferably, the reinforcing element 4 is a filament of a relatively stiff plastics, such as polyester or nylon, but it could be a metal wire. The filament 4 is of rectangular section being 0.25 mm thick by 0.5 mm wide for the larger diameter tubular members. Alternatively, a filament of circular section could be used.

The next station in the apparatus is a first coating station 10 where the tubular member 2 with its reinforcing element 4 is given a layer 11 (FIG. 2) of a flexible plastics material, preferably of the same material as that of the tubular member. The layer 11 is applied so that it just covers the reinforcing element 4 by a depth of about 0.1 mm, although it is only necessary for this coating to be applied to a level substantially level with the outer surface of the reinforcing element. This layer 11 helps retain and embed the reinforcing element and also forms a smooth surface along the tubular member 2. The layer 11 is preferably applied by co-extrusion.

Figure 2:
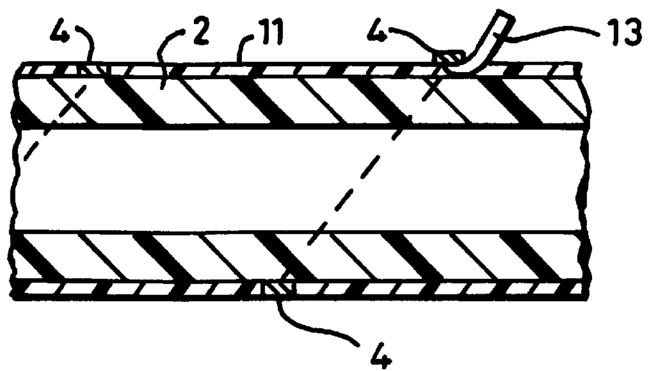
FIG. 2 is a sectional side-elevation view of a part of the tubular member at a preliminary stage of manufacture.

At the next station 12, the reinforcing element 4 is removed from regions along the tubular member 2. This may be done in various ways, but preferably a pick 13 is hooked beneath the reinforcing filament 4 from the outside of the tubular member 2, the pick being pulled outwardly to pull the filament out through the coating 11, as shown in FIG. 2. Because the depth of the layer 11 over the filament 4 is very thin, the coating provides little impediment to removal of the filament. The filament 4 is cut close to the surface of the tubular member 2 so that any short projecting part of the filament springs back in by its resilience. Typically, for the larger diameter tubular members, the reinforcing filament 4 is removed to form reinforced regions 15 about 300 mm long separated by unreinforced regions 16 of about 50 mm. The reinforcing filament 4 may be removed manually or automatically.

Figure 3:
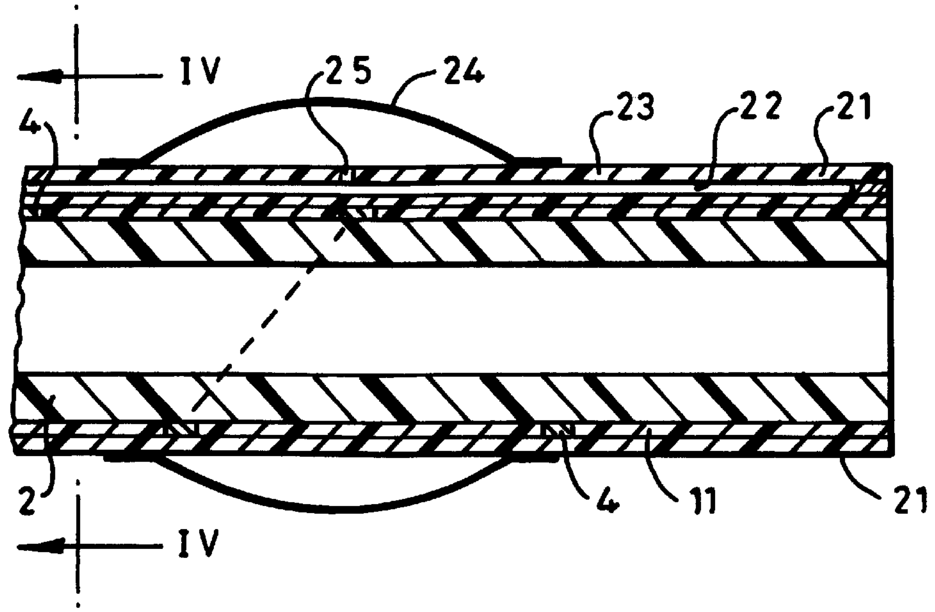
FIG. 3 is a sectional side-elevation view of a part of a finished tube.
Figure 4:
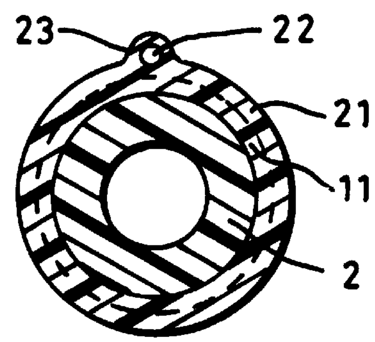
FIG. 4 is a transverse cross-section of the finished tube along the line IV—IV of FIG. 3.

Immediately after the station 12 where the reinforcing filament 4 is removed, there is a second coating station 20. At this station 20, a second layer 21 is co-extruded along the entire length of the tubular member 2, over both the reinforced regions 15 and the unreinforced regions 16, as shown in FIGS. 3 and 4. The second layer 21 is preferably of the same material as the first layer 11 and is applied to approximately the same depth. The second coating station 20 extrudes a longitudinal minor lumen 22 within the outer coating 21, along the length of the tubular member, such as in a longitudinal rib 23 projecting outwardly. The inflation lumen 22 is used to make connection with an inflatable cuff 24 assembled towards one end of the finished tubes in the usual way, the lumen communicating with the interior of the cuff via an opening 25 cut into the lumen from outside the tube.

The next station 26 is a cutting station where the tubular member 2 is cut laterally into discrete lengths, or tubes 30. In most cases, the cut is made at some point approximately midway along the unreinforced regions 16 so that both ends of the tubes 30 have unreinforced end regions. For some tubes, however, it may be preferable for there to be an unreinforced region at one end only, in which case, the cut is made at the junction between the reinforced and unreinforced regions. Subsequently, the tubes 30 are subject to various conventional finishing operations, such as end forming, attachment of the inflatable cuff 24 or the like.

The method of forming the tubes 30, therefore, comprises the steps of winding a reinforcing element about a tubular member, applying a first coating to a level substantially equal to the outer surface of the reinforcing element, removing the reinforcing element from selected regions along the tubular member to form reinforced and unreinforced regions, applying a second coating over the reinforced and unreinforced regions, and then cutting the tubular member in the unreinforced regions to form tubes with at least one unreinforced end.

It has been found, by applying a preliminary layer 11 prior to removing the reinforcing element 4 and then applying a subsequent coating 21 after removal of the reinforcement, that the outer surface of the finished tubes can be appreciably smoother than if just a single coating were applied, after removal. Also, because the tubular member fed to the second coating station 20 has a substantially smooth outer surface, it enables the outer coating to be applied by an extrusion process, thereby enabling additional features, such as an inflation lumen, to be incorporated into the outer lumen.

The method of forming the tubes need not be a continuous process, as described above. At various stages, the method could be interrupted and subsequent steps carried out later. For example, the tubular member could be fed onto a reel after the first layer and the subsequent operations carried out at a different location, or at a different time.

What I claim is:

1. A method of forming a reinforced tube comprising the steps, performed in the sequence stated hereinafter, of: providing a flexible tubular member; winding a reinforcing element helically onto an outer surface of said flexible tubular member; then applying a first layer of a flexible material to said tubular member substantially level with an outer surface of said reinforcing element; thereafter removing said reinforcement element from selected regions of said tubular member to form unreinforced regions intermediate reinforced regions along said tubular member; subsequently applying a second layer of a flexible material over said reinforced and unreinforced regions; and then cutting said tubular member in said unreinforced regions to divide said tubular member into tubes having at least one unreinforced end.

2. A method according to claim 1, wherein said reinforcing element is of rectangular section.

3. A method according to claim 1, wherein said reinforcing element is of a plastics material.

4. A method according to claim 1, wherein said first layer is applied by coextrusion.

5. A method according to claim 1, wherein said first layer is of the same material as said tubular member.

6. A method according to claim 1, wherein said second layer is applied by coextrusion.

7. A method according to claim 1, wherein said second layer is of the same material as said first layer.

8. A method according to claim 1, wherein said second layer is formed with a lumen extending along its length.

9. A method according to claim 8 including the step of applying an inflatable cuff to each tube after cutting said tubular member into tubes.

10. A method according to claim 1, wherein the reinforcement element is removed using a pick.

11. A method according to claim 1, wherein said tubular member is cut in said unreinforced regions between the ends of said unreinforced regions so that each tube has two unreinforced ends.

12. A method of forming a reinforced tube comprising the steps, performed in the sequence stated hereinafter, of: providing a flexible tubular member; winding a reinforcing element helically onto an outer surface of said flexible tubular member; then applying a first layer of a flexible material to said tubular member; thereafter removing said reinforcement element from selected regions of said tubular member to form unreinforced regions intermediate reinforced regions along said tubular member; subsequently extruding a second layer of a flexible material over said reinforced and unreinforced regions, said second layer including a lumen extending longitudinally; then cutting said tubular member in said unreinforced regions to divide said tubular member into tubes having at least one unreinforced end; and then applying an inflatable cuff to each said tube.

13. A method of forming a reinforced tube comprising the steps of: providing a flexible tubular member; winding a reinforcing element onto an outer surface of said flexible tubular member; applying a first layer of a flexible material to said tubular member substantially level with an outer surface of said reinforcing element; pulling said reinforcement element through said first layer in a selected region and cutting said reinforcement element to form unreinforced regions intermediate reinforced regions along said tubular member; extruding a second layer of a flexible material over said reinforced and unreinforced regions, said second layer including a longitudinal lumen; cutting said tubular member in said unreinforced regions between the ends of said unreinforced regions to divide said tubular member into tubes having an unreinforced region at both ends; and applying an inflatable cuff to each tube towards one of said unreinforced ends.

* * * * *